US012796897B2

(12) United States Patent
Govari et al.

(10) Patent No.: US 12,796,897 B2
(45) Date of Patent: Nov. 17, 2026

(54) ENT GUIDEWIRE

(71) Applicant: BIOSENSE WEBSTER (ISRAEL) LTD., Yokneam (IL)

(72) Inventors: Assaf Govari, Haifa (IL); Andres Claudio Altmann, Haifa (IL); Yehuda Algawi, Binyamina (IL); Ilya Sitnitsky, Nahariya (IL); Vadim Gliner, Haifa (IL); Yair Palti, Herzelia (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 169 days.

(21) Appl. No.: 18/788,248

(22) Filed: Jul. 30, 2024

(65) Prior Publication Data

US 2024/0382075 A1 Nov. 21, 2024

Related U.S. Application Data

(62) Division of application No. 16/943,789, filed on Jul. 30, 2020, now Pat. No. 12,102,293.

(Continued)

(51) Int. Cl.
*A61B 18/00* (2006.01)
*A61B 1/00* (2006.01)

(Continued)

(52) U.S. Cl.
CPC .......... *A61B 1/005* (2013.01); *A61B 1/00097* (2022.02); *A61B 1/0052* (2013.01);

(Continued)

(58) Field of Classification Search
None
See application file for complete search history.

(56) References Cited

U.S. PATENT DOCUMENTS 5,228,441 A * 7/1993 Lundquist .......... A61B 18/1492 607/116
5,255,668 A 10/1993 Umeda (Continued)

FOREIGN PATENT DOCUMENTS

EP 3453310 A2 3/2019
JP S4735348 Y1 10/1972

(Continued)

OTHER PUBLICATIONS

International Search Report and Written Opinion, received for PCT Application No. PCT/IL2019/000002, mailed on Jan. 18, 2021, 18 pages.

(Continued)

*Primary Examiner* — Joanne M Rodden
*Assistant Examiner* — Nicholas S Borsch

(57) ABSTRACT

A guidewire, consisting of a flexible biocompatible tube, having a tube distal end, the tube containing an internal lumen and being configured to be inserted into an orifice of a body of a living subject. A planar resilient strip is inserted into the internal lumen, the strip having a strip proximal end and a strip distal end fixed to the tube distal end. A coil spring is fixed to the strip proximal end so that an axis of symmetry of the coil is coplanar with the strip, the coil spring containing a coil lumen. A wire is threaded through the coil lumen and has a termination fixed to the strip distal end, so that pulling on the wire causes the strip and the tube to bend.

8 Claims, 9 Drawing Sheets

Related U.S. Application Data

(60) Provisional application No. 62/893,924, filed on Aug. 30, 2019.

(51) Int. Cl.

| | |
|---|---|
| ***A61B 1/005*** | (2006.01) |
| ***A61B 1/07*** | (2006.01) |
| ***A61B 1/227*** | (2006.01) |
| ***A61B 1/233*** | (2006.01) |
| ***A61B 1/273*** | (2006.01) |
| ***A61B 17/00*** | (2006.01) |
| ***A61B 18/14*** | (2006.01) |
| ***A61B 90/00*** | (2016.01) |
| ***A61B 90/30*** | (2016.01) |

(52) U.S. Cl.
CPC ................ *A61B 1/07* (2013.01); *A61B 1/227* (2013.01); *A61B 1/233* (2013.01); *A61B 1/273* (2013.01); *A61B 18/1492* (2013.01); *A61B 90/37* (2016.02); *A61B 2018/00059* (2013.01); *A61B 2018/0072* (2013.01); *A61B 2018/00732* (2013.01); *A61B 2018/00827* (2013.01); *A61B 2018/00875* (2013.01); *A61B 2018/00982* (2013.01); *A61B 2018/1467* (2013.01); *A61B 2090/3762* (2016.02)

(56) References Cited

U.S. PATENT DOCUMENTS

| | | | | |
|---|---|---|---|---|
| 5,431,649 A | | 7/1995 | Mulier et al. | |
| 5,741,249 A | | 4/1998 | Moss et al. | |
| 6,032,070 A | * | 2/2000 | Flock | A61B 90/36 600/476 |
| 7,668,585 B2 | * | 2/2010 | Green | A61B 5/0535 600/428 |
| 2001/0018585 A1 | * | 8/2001 | Mcgovern | A61B 18/1485 606/41 |
| 2003/0163040 A1 | | 8/2003 | Gildenberg | |
| 2005/0267522 A1 | | 12/2005 | Yassinzadeh et al. | |
| 2006/0095025 A1 | | 5/2006 | Levine et al. | |
| 2006/0146172 A1 | * | 7/2006 | Jacobsen | H04N 23/50 348/340 |
| 2006/0184060 A1 | * | 8/2006 | Belalcazar | A61B 5/0537 600/547 |
| 2006/0241445 A1 | | 10/2006 | Altmann et al. | |
| 2010/0036405 A1 | | 2/2010 | Giordano et al. | |
| 2010/0106154 A1 | | 4/2010 | Harlev et al. | |
| 2011/0009694 A1 | | 1/2011 | Ouyang et al. | |
| 2013/0079645 A1 | * | 3/2013 | Amirana | A61B 1/05 600/479 |
| 2013/0324989 A1 | | 12/2013 | Leung et al. | |
| 2015/0157387 A1 | | 6/2015 | Ouyang et al. | |
| 2016/0310211 A1 | * | 10/2016 | Long | A61B 18/1492 |
| 2017/0007096 A1 | * | 1/2017 | Suzuki | A61B 1/051 |
| 2018/0153437 A1 | * | 6/2018 | Schwartz | A61B 18/1492 |
| 2021/0059746 A1 | | 3/2021 | Govari et al. | |

FOREIGN PATENT DOCUMENTS

| | | |
|---|---|---|
| JP | H04244131 A | 9/1992 |
| JP | H07163514 A | 6/1995 |
| JP | H09140801 A | 6/1997 |
| WO | 2012124391 A1 | 9/2012 |

OTHER PUBLICATIONS

Amorós-Figueras et al., "Recognition of Fibrotic Infarct Density by the Pattern of Local Systolic-Diastolic Myocardial Electrical Impedance", Frontiers in Physiology, vol. 7, pp. 1-10, Aug. 31, 2016.

* cited by examiner

ENT GUIDEWIRE

CROSS-REFERENCE TO RELATED APPLICATIONS

This patent application is a divisional application of U.S. patent application Ser. No. 16/943,789 filed on Jul. 30, 2020, which claims the benefit of U.S. Provisional Application No. 62/893,924 filed Aug. 30, 2019, which is incorporated herein by reference.

FIELD OF THE INVENTION

This invention relates generally to surgical tools, and specifically to a guidewire which may be used for an ENT (ear, nose, and throat) investigation.

BACKGROUND OF THE INVENTION

Inspecting the sinuses of a person is typically difficult because the sinuses have narrow openings and also vary considerably from person to person. To alleviate the difficulty, an inspection tool should be as narrow and as flexible as possible, while still being rigid enough for a physician to navigate the tool to a desired location.

SUMMARY OF THE INVENTION

An embodiment of the present invention provides a guidewire, including:

a flexible biocompatible tube, having a tube distal end, the tube containing an internal lumen and being configured to be inserted into an orifice of a body of a living subject;

a planar resilient strip inserted into the internal lumen, the strip having a strip proximal end and a strip distal end fixed to the tube distal end;

a coil spring fixed to the strip proximal end so that an axis of symmetry of the coil is coplanar with the strip, the coil spring containing a coil lumen; and a wire, threaded through the coil lumen and having a termination fixed to the strip distal end, so that pulling on the wire causes the strip and the tube to bend.

In a disclosed embodiment the guidewire includes a camera mounted on an upper surface of the strip at the strip distal end, the camera being configured to image a scene internal to the body.

In a further disclosed embodiment the guidewire includes a pair of biocompatible electrodes formed on an outer surface of the flexible biocompatible tube at the tube distal end, the pair of electrodes being configured to contact tissue internal to the body.

Typically, the strip has a rectangular cross-section, and consists of super-elastic material.

In a yet further disclosed embodiment the coil spring consists of a tension spring having coils contacting each other when the spring is unloaded.

In an alternative embodiment the strip has a first surface and a second surface opposite the first surface, and the wire is threaded between the first surface and the coil spring and is fixed to the first surface at the strip distal end, so that pulling on the wire causes the strip and the tube to bend in a bending direction defined by a vector from the second surface to the first surface. The guidewire may include a further wire threaded between the second surface and the coil spring and fixed to the second surface at the strip distal end, so that pulling on the further wire causes the strip and the tube to bend in a further direction opposite the direction defined by the vector.

There is further provided, according to an embodiment of the present invention, apparatus, including:

a guidewire, having:

a flexible biocompatible tube, having a tube distal end, the tube containing an internal lumen and being configured to be inserted into an orifice of a body of a living subject;

a resilient strip inserted into the internal lumen, the strip having a strip proximal end and a strip distal end fixed to the tube distal end;

a coil spring fixed to the strip proximal end so that an axis of symmetry of the coil is coplanar with the strip, the coil spring containing a coil lumen;

a wire, threaded through the coil lumen and having a termination fixed to the strip distal end, so that pulling on the wire causes the strip and the tube to bend; and a first and a second fiber optic having distal ends located in proximity to the tube distal end, and configured to provide illumination into the body; and a processor, including an optics module, coupled to at least one of the first and the second fiber optics, configured to generate the illumination as photo-exciting illumination.

In a disclosed embodiment the optics module is configured to record returning excited photoluminescent illumination produced in response to the photo-exciting illumination. Typically, the first fiber optic is coupled so as to radiate the photo-exciting illumination, and the second fiber optic is coupled to receive the returning excited photoluminescent illumination after filtration of the photo-exciting illumination.

In a further disclosed embodiment the guidewire includes a pair of biocompatible electrodes formed on an outer surface of the flexible biocompatible tube at the tube distal end, and the processor has a module configured to investigate characteristics of tissue contacted by the electrodes by injecting an electrical signal from the electrodes into the tissue. The injected signal may have an applied predetermined voltage and the module may be configured to measure an impedance of the contacted tissue in response to a current generated by the voltage so as to provide an indication if the tissue is vital or fibrotic. Alternatively or additionally the injected signal may be pulses applied at a frequency greater than a heart rate of the living subject, so as to electrically stimulate the contacted tissue, and so as to provide an indication if the tissue is vital.

There is further provided, according to an embodiment of the present invention, a method, including:

inserting a guidewire, consisting of a flexible biocompatible tube having a tube distal end and a camera fixed in proximity to the distal end, into an orifice of a body of a living subject;

tracking a position of the camera within the body;

acquiring an image of internal elements of the body with the tracked camera;

in response to the tracked position of the camera, combining the image of the internal elements with a computerized tomographic (CT) image of the internal elements so as to form a combined image; and presenting a combined image on a screen.

Typically, combining the image includes overlaying the camera image onto the CT image using projective texture mapping. Alternatively or additionally, combining the image includes incorporating three-dimensional information derived from pixels of the CT image into the camera image.

There is further provided, according to an embodiment of the present invention, a method, including:

inserting a guidewire, consisting of a flexible biocompatible tube having a tube distal end and a first and a second fiber optic having distal ends located in proximity to the tube distal end, into an orifice of a body of a living subject;

radiating photo-exciting illumination via the first fiber optic into the body;

receiving, via the second fiber optic, returning excited photoluminescent illumination after filtration of the photo-exciting illumination; and providing an indication of reception of the returning excited photoluminescent illumination.

The indication may be indicative of the tube distal end being in proximity to tissue of the body that has taken up an injected photoluminescent chemical.

There is further provided, according to an embodiment of the present invention, a method, including:

inserting a guidewire, consisting of a flexible biocompatible tube having a tube distal end and a pair of biocompatible electrodes formed on an outer surface of the flexible biocompatible tube at the tube distal end, into an orifice of a body of a living subject so that the electrodes contact tissue therein;

applying a predetermined voltage via the electrodes to the contacted tissue;

measuring a current generated in response to the predetermined voltage so as to measure an impedance of the contacted tissue; and providing an indication if the tissue is vital or fibrotic in response to the impedance.

The predetermined voltage may be applied at a frequency which does not stimulate the tissue.

There is further provided, according to an embodiment of the present invention, a method, including:

inserting a guidewire, consisting of a flexible biocompatible tube having a tube distal end and a pair of biocompatible electrodes formed on an outer surface of the flexible biocompatible tube at the tube distal end, into an orifice of a body of a living subject so that the electrodes contact tissue therein;

applying pulses via the electrodes at a frequency greater than a heart rate of the living subject, so as to electrically stimulate the contacted tissue; and in response to the stimulation, providing an indication if the tissue is vital.

The indication may include observing visible motion of the contacted tissue.

There is further provided, according to an embodiment of the present invention, a method, including:

providing a flexible biocompatible tube, having a tube distal end, the tube containing an internal lumen and being configured to be inserted into an orifice of a body of a living subject;

inserting a planar resilient strip into the internal lumen, the strip having a strip proximal end and a strip distal end fixed to the tube distal end;

fixing a coil spring to the strip proximal end so that an axis of symmetry of the coil is coplanar with the strip, the coil spring containing a coil lumen; and threading a wire through the coil lumen, the wire having a termination fixed to the strip distal end, so that pulling on the wire causes the strip and the tube to bend.

There is further provided, according to an embodiment of the present invention, a method, including:

providing a guidewire, by:

providing a flexible biocompatible tube, having a tube distal end, the tube containing an internal lumen and being configured to be inserted into an orifice of a body of a living subject, inserting a resilient strip into the internal lumen, the strip having a strip proximal end and a strip distal end fixed to the tube distal end, fixing a coil spring to the strip proximal end so that an axis of symmetry of the coil is coplanar with the strip, the coil spring containing a coil lumen, threading a wire through the coil lumen, the wire having a termination fixed to the strip distal end, so that pulling on the wire causes the strip and the tube to bend, and locating distal ends of a first and a second fiber optic in proximity to the tube distal end, the fiber optics being configured to provide illumination into the body; and generating the illumination as photo-exciting illumination.

There is further provided, according to an embodiment of the present invention, apparatus, including:

a guidewire, consisting of a flexible biocompatible tube having a tube distal end configured to be inserted into an orifice of a body of a living subject;

a camera fixed in proximity to the tube distal end; and a processor configured:

to track a position of the camera within the body, to acquire an image of internal elements of the body with the tracked camera, in response to the tracked position of the camera, to combine the image of the internal elements with a computerized tomographic (CT) image of the internal elements so as to form a combined image, and to present a combined image on a screen.

There is further provided, according to an embodiment of the present invention, apparatus, consisting of:

a guidewire, including a flexible biocompatible tube having a tube distal end configured to be inserted into an orifice of a body of a living subject;

a first and a second fiber optic having distal ends located in proximity to the tube distal end; and a processor configured:

to radiate photo-exciting illumination via the first fiber optic into the body, to receive, via the second fiber optic, returning excited photoluminescent illumination after filtration of the photo-exciting illumination; and to provide an indication of reception of the returning excited photoluminescent illumination.

There is further provided, according to an embodiment of the present invention, apparatus, consisting of:

a guidewire, including a flexible biocompatible tube having a tube distal end configured to be inserted into an orifice of a body of a living subject;

a pair of biocompatible electrodes, formed on an outer surface of the flexible biocompatible tube at the tube distal end, configured to contact tissue of the body; and a processor, configured:

to apply a first predetermined voltage via the electrodes to the contacted tissue, to measure a current generated in response to the first predetermined voltage so as to measure an impedance of the contacted tissue, and to provide an indication if the tissue is vital or fibrotic in response to the impedance.

There is further provided, according to an embodiment of the present invention, apparatus, consisting of:

- a guidewire, including a flexible biocompatible tube having a tube distal end configured to be inserted into an orifice of a body of a living subject;
- a pair of biocompatible electrodes, formed on an outer surface of the flexible biocompatible tube at the tube distal end, configured to contact tissue of the body; and
- a processor, configured:
- to apply pulses via the electrodes at a frequency greater than a heart rate of the living subject, so as to electrically stimulate the contacted tissue; and
- in response to the stimulation, to provide an indication if the tissue is vital.

The present disclosure will be more fully understood from the following detailed description of the embodiments thereof, taken together with the drawings, in which:

DETAILED DESCRIPTION OF EMBODIMENTS

Overview

Embodiments of the present invention provide a guidewire, which by virtue of its internal construction, is sufficiently rigid so as to be able to be manipulated at its proximal end by a physician, while being narrow enough so that the distal end may be inserted deeply into sinuses of a patient. In addition, the internal construction enables the distal end to be controllably bent by the physician in two directions.

The guidewire is formed from a narrow biocompatible tube having an internal lumen. A resilient strip is inserted into the lumen, and a distal end of the strip is fixed to the distal end of the tube. A coil spring is fixed to the proximal end of the strip, and the combination of the tube, together with the internal strip and coil, provide the required blend of rigidity and, at the distal end, flexibility, needed for the guidewire to penetrate into a patient's sinuses.

The bending of the distal end is controlled by two separate wires which are threaded through the coil and which are then fixed to the strip distal end. Pulling on one wire deflects the guidewire in one direction; pulling on the other wire deflects in the opposite direction.

A camera, fiber optics, and electrodes are incorporated into the distal end of the guidewire. These entities enable the guidewire to be used to visually inspect tissue of the sinuses in proximity to the guidewire distal end, as well as to characterize the tissue.

DETAILED DESCRIPTION

In the following, all directional references (e.g., upper, lower, upward, downward, left, right, top, bottom, above, below, vertical, and horizontal) are only used for identification purposes to aid the reader's understanding of the present invention, and do not create limitations, particularly as to the position, orientation, or use of embodiments of the invention.

Figure 1:
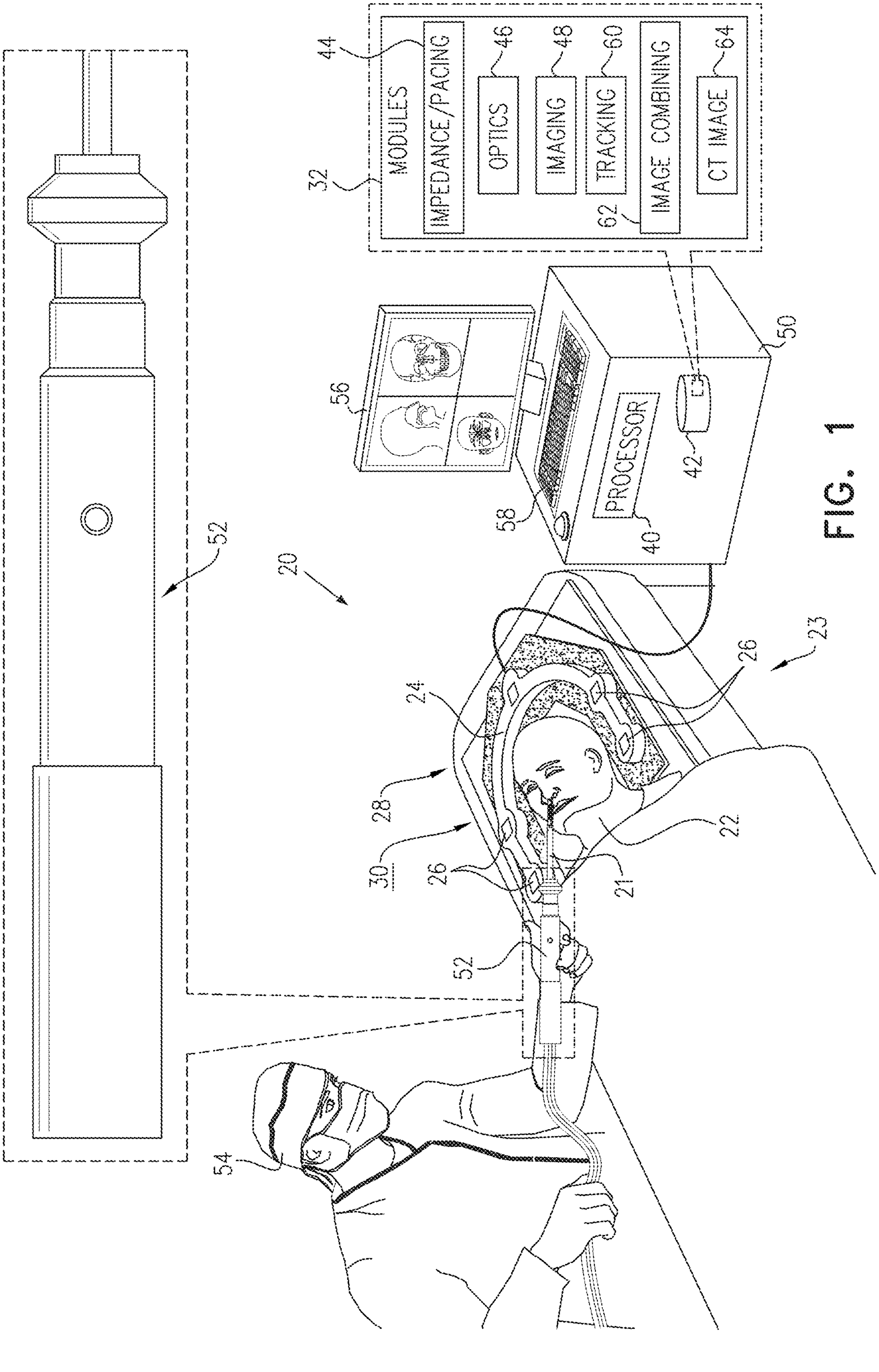
FIG. 1 is a schematic illustration of an ENT (ear, nose, and throat) system using a guidewire, according to an embodiment of the present invention.

Reference is now made to FIG. 1, which is a schematic illustration of an ENT (ear, nose, and throat) system 20 using a guidewire 21, according to an embodiment of the present invention. In the following description a physician 54 is assumed, by way of example, to use guidewire 21 for investigation of tissues of a patient 22, typically prior to performing a sinuplasty procedure on the patient. However, it will be appreciated that guidewire 21 may be used just for investigating tissues of patient 22. As is described in more detail below, guidewire 21 comprises a magnetic sensor 28 in its distal end, and the sensor is tracked during use of the guidewire by a magnetic tracking system 23.

Tracking system 23 comprises a magnetic radiator assembly 24 which is positioned beneath the patient's head. Assembly 24 comprises magnetic field radiators 26 which are fixed in position and which transmit alternating sinusoidal magnetic fields into a region 30 wherein the head of patient 22 is located. By way of example, radiators 26 of assembly 24 are arranged in an approximately horseshoe shape around the head of patient 22. However, alternate configurations for the radiators of assembly 24 will be apparent to those having ordinary skill in the art, and all such configurations are assumed to be comprised within the scope of the present invention. The Carto® system produced by Biosense Webster, of 33 Technology Drive, Irvine, CA 92618 USA, uses a tracking system similar to that described herein for finding the location and orientation of a coil in a region irradiated by magnetic fields.

Elements of system 20, including radiators 26, are controlled by a system processor 40. The processor is also configured to receive the signals originating in magnetic sensor 28, and to process the signals to derive location and orientation values for the sensor. Processor 40 may be mounted in a console 50, which comprises operating controls 58 that typically include a keypad and/or a pointing device such as a mouse or trackball. Console 50 connects to the radiators via a cable and/or wirelessly. Physician 54 uses operating controls 58 to interact with the processor while performing the procedures described herein using system 20. While performing the procedures, the processor may present results of the procedures on a screen 56.

Processor 40 uses software stored in a memory 42 to operate system 20. The software may be downloaded to processor 40 in electronic form, over a network, for example, or it may, alternatively or additionally, be provided and/or stored on non-transitory tangible media, such as magnetic, optical, or electronic memory.

Processor 40 uses the software, inter alia, to operate magnetic radiators 26 of assembly 24, and to analyze the signals received from magnetic sensor 28. As stated above the radiators transmit sinusoidal alternating magnetic fields of different frequencies into region 30, including the head of patient 22, and the fields from the radiators induce signals in magnetic sensor 28. The processor analyzes the signals from sensor 28 to determine location and orientation coordinates for the sensor in a frame of reference defined by radiator assembly 24.

Also stored in memory 42 is a software module bank 32, comprising an impedance/pacing module 44, an optics module 46, a camera imaging module 48, a tracking module 60, and an image combining module 62. Tracking module 60 communicates with processor 40 so as to provide the functionality described above for assembly 24. The functions of the other modules in bank 32 are explained in detail below. In addition, memory 42 stores a computerized tomography (CT) image 64 of patient 22. CT image 64 is herein assumed to be produced by fluoroscopy.

To insert guidewire 21 into the patient, physician 54 uses a handle 52 attached to a proximal end of the guidewire. Handle 52 comprises controls which enable the physician to manipulate the guidewire, and to activate functions performed by the guidewire.

Figure 2A:
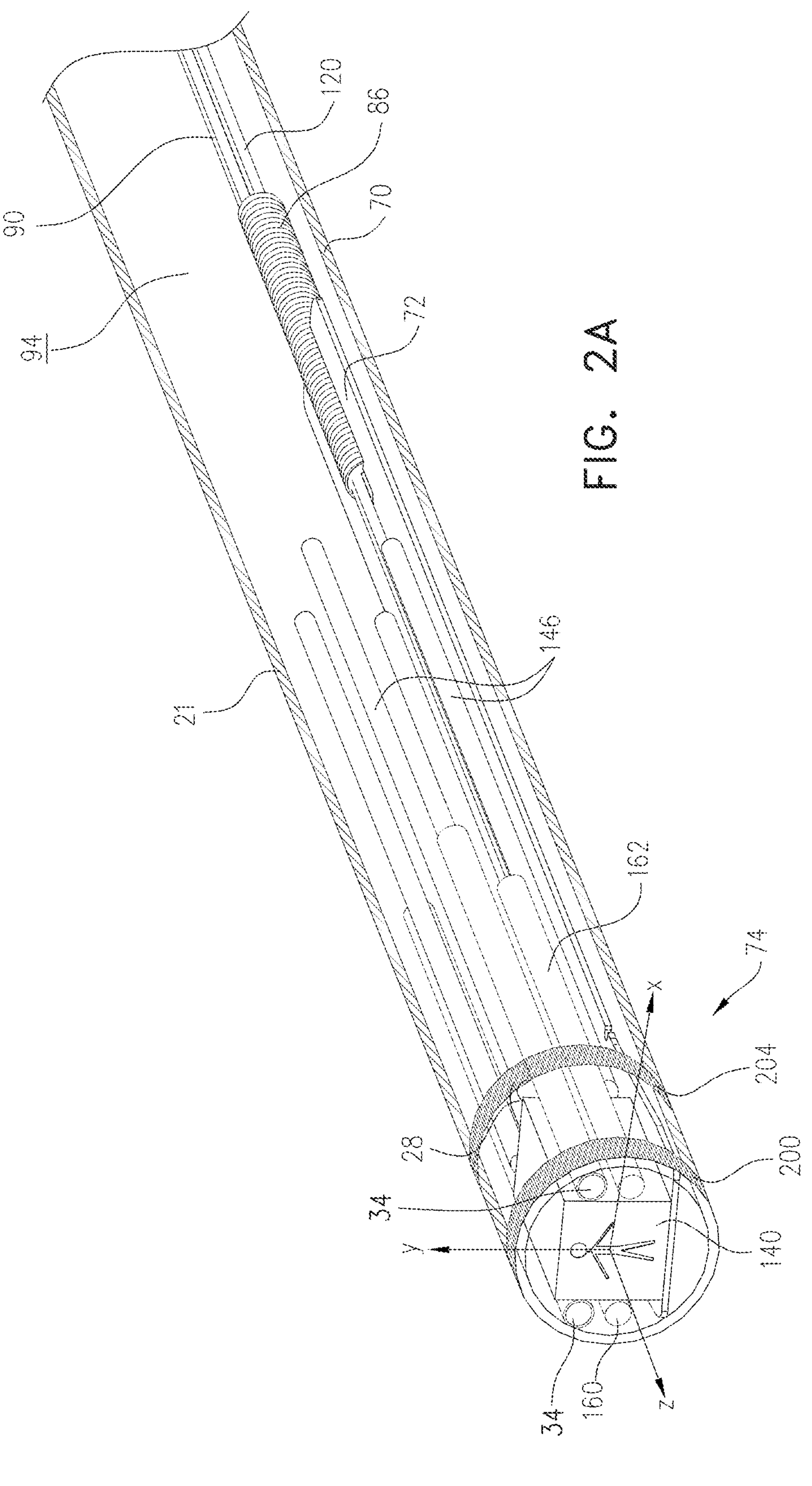
FIGS. 2A, 2B, and 2C are schematic diagrams illustrating the guidewire, according to an embodiment of the present invention.
Figure 2B:
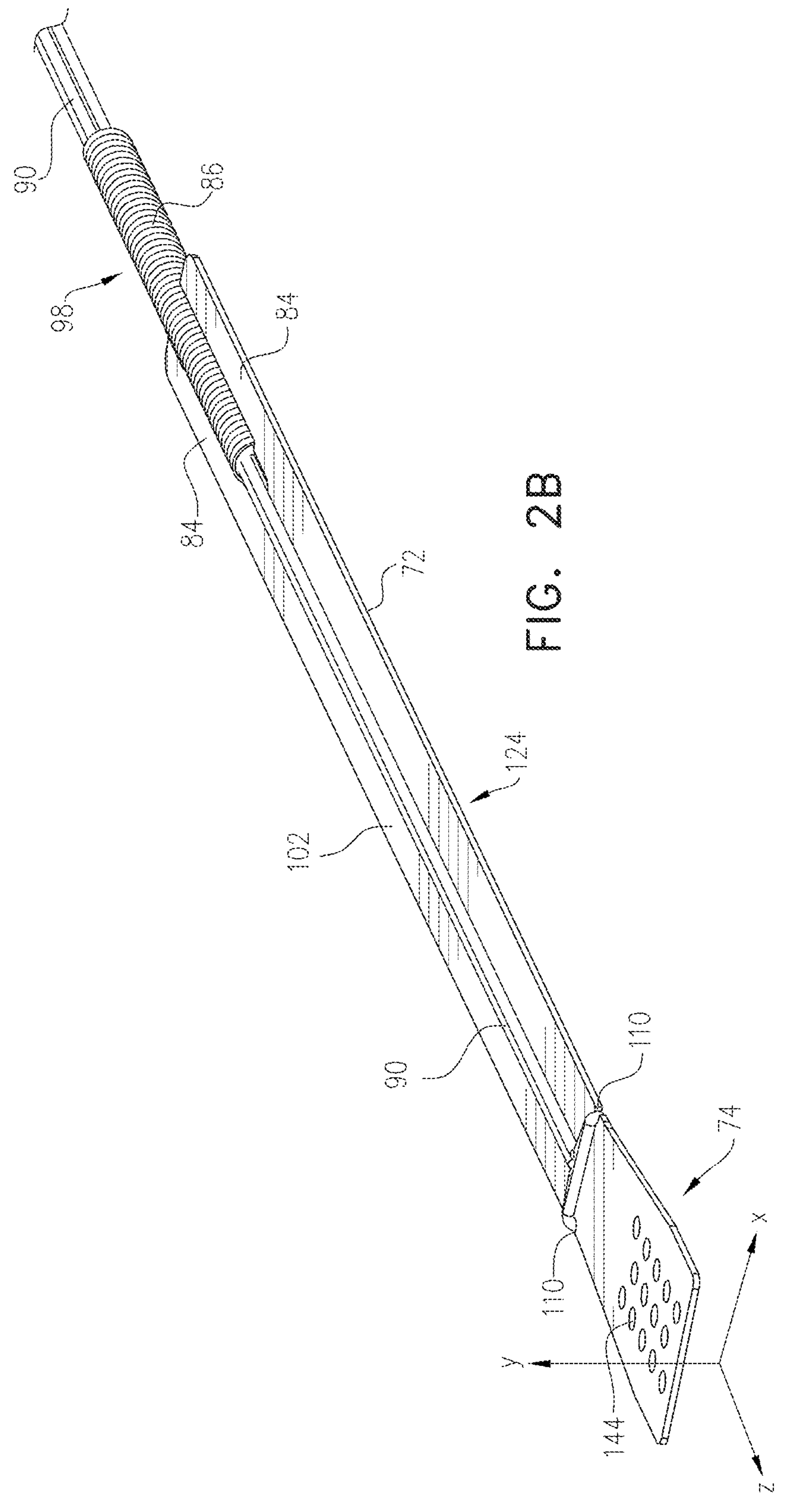
Figure 2C:
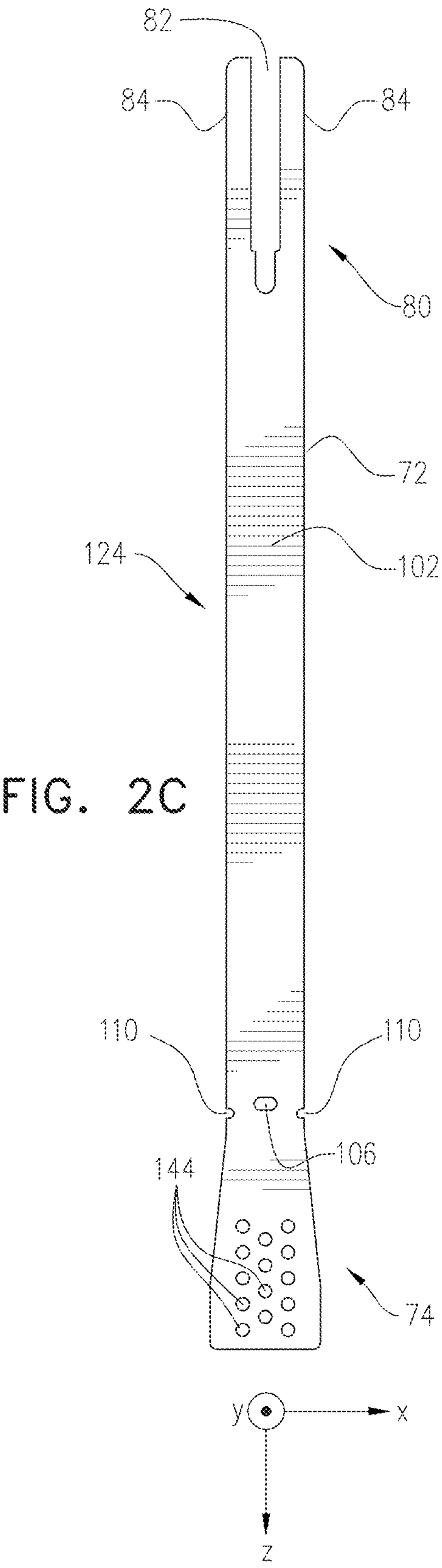

FIGS. 2A, 2B, and 2C are schematic diagrams illustrating guidewire 21, according to an embodiment of the present invention. FIG. 2A is a schematic perspective view of the guidewire, which comprises an external biocompatible flexible tube 70, typically formed from a plastic such as polyimide. Tube 70 is shown as transparent in FIG. 2A. In one embodiment external tube 70 has an outer diameter of 2.1 mm, and an inner diameter of 1.9 mm. FIGS. 2B and 2C illustrate internal elements of the guidewire.

At the distal end of tube 70, and inside the tube, there is a planar resilient strip 72. Strip 72 is typically formed from a super-elastic material such as nitinol, and is generally planar with a rectangular shape, except as described herein. In one embodiment, the strip has dimensions with the following ranges: length 15-25 mm, width 1-1.5 mm, thickness 0.6-1.5 mm. Strip 72 is also referred to herein as insert 72. FIG. 2C illustrates insert 72 in plan view. As illustrated in FIG. 2C, insert 72 is slightly widened at its distal end 74, so that when positioned in tube 70 it contacts the tube, and it is fixedly connected thereto with glue.

In the following description, for clarity guidewire 21 is assumed to define a set of orthogonal xyz axes, where the z axis corresponds to the axis of symmetry of tube 70, the x-axis is orthogonal to the z-axis so that insert 72 is in an xz plane, and the y-axis is orthogonal to the insert.

Insert 72 comprises, at its proximal end 80, an opening 82 between two arms 84 formed in the insert. Opening 82 is configured to receive a coil spring 86, and when the coil is inserted into the opening, it is held in place by the elasticity of arms 84. Coil spring 86 is typically a tension spring, having coils contacting each other when the spring is unloaded. In one embodiment the spring has an outside diameter of 0.48 mm. On insertion, the spring is also held fixedly to arms 84 by glue and/or by welding, and the spring is positioned in the opening so that it is symmetrical with respect to insert 82, i.e., so that an axis of symmetry of the spring is coplanar with planar strip 72.

A first wire 90 is threaded from a first wire control in handle 52, through a lumen 94 contained in tube 70, and through a central lumen 98 contained in spring 86. Wire 90 traverses an upper surface 102 of insert 72 to an opening 106 at distal end 74 of the insert. Wire 90 threads through opening 106, wraps round distal end 74 via indentations 110 in the distal end, and returns to the first wire control of handle 52 by again traversing upper surface 102 and central lumen 98 of the coil spring. Thus, first wire 90 is held by its two ends by the first wire control in handle 52, and is fixed to distal end 74 of insert 72 at opening 106.

A second wire 120 is threaded from a second wire control in handle 52, through lumen 94 and through central lumen 98. Wire 120 traverses a lower surface 124 of insert 72 to opening 106 at the distal end of the insert. As for wire 90, wire 120 threads through opening 106, wraps round distal end 74 via indentations 110 in the distal end, and returns to the second wire control of handle 52 by again traversing lower surface 124 and the central lumen of the coil spring. Thus, second wire 120 is also held by its two ends by the second wire control in handle 52, and is fixed to distal end 74 of insert 72 at opening 106.

The first wire control in handle 52 may be used to pull on first wire 90, i.e., on the two ends of the wire which are connected to the control, while second wire 120 is free to move. It will be understood that pulling first wire 90 causes distal end 74 of the insert, and thus the distal end of guidewire 21, to bend upwards, i.e., in a direction defined by a vector from lower surface 124 to upper surface 102.

Similarly, the second wire control in handle 52 may be used to pull on the two ends of second wire 120, while first wire 90 is free to move. In this case pulling second wire 120 causes distal end 74 of the insert, and thus the distal end of guidewire 21, to bend downwards, i.e., in a direction opposite to that of the vector described above.

The combination of coil spring 86 fixedly connected to planar resilient insert 72 enables guidewire 21 to be deflected in an upward or downward direction, while preventing the guidewire from deflecting sideways. The combination also provides the guidewire with sufficient rigidity so that, absent pulls from wires 90 and 120, it remains in an undeflected form. In embodiments of the present invention the guidewire may have a bending radius between approximately 2 mm and approximately 5 mm, forming a bend angle of up to approximately 160°.

While a single planar insert alone could provide the functionality described herein of the combination, the combination of the coil spring with the plane insert 72 significantly reduces the size needed for the insert, and thus of the guidewire, compared to that needed for the single insert alone. Furthermore, the lumen of the coil spring acts as a guide for wires 90 and 120, whereas if a single planar insert were used a guide providing the same functionality as the lumen of the spring would have to be made available.

FIG. 2A illustrates the position of sensor 28, which is assumed to comprise a single axis coil having its axis of symmetry parallel to the z axis. Sensor 28 is mounted, by gluing, onto upper surface 102. As is also illustrated in FIG. 2A, guidewire 21 comprises irrigation tubes 34, and typically physician 54 uses a control in handle 52 to set the flow of irrigation fluid through the irrigation tubes.

Guidewire 21 comprises a camera 140, mounted on upper surface 102 of the distal end of insert 72. The camera is attached to insert 72 by glue through holes 144 in the insert distal end. Power and driving signals for the camera, together with imaging signals generated by the camera, are conveyed by cabling connecting to the camera, via handle 52. The cabling is indicated schematically in FIG. 2A by lines 146. The power and driving signals are provided by imaging module 48, which also, typically together with processor 40, receives the imaging signals generated by the camera so as to provide an image of the scene viewed by the camera on screen 56.

Optics Module 46

Illumination in the visible spectrum for camera 140 is provided by a pair of fiber optics 160, 162, only the distal ends of which are shown in FIG. 2A. In some embodiments, the illumination is provided by LEDs (light emitting diodes). The visible spectrum illumination is generated by optics module 46.

Optics module 46 is also configured to generate photo-exciting illumination, and to record returning excited photoluminescent illumination, after filtering out the exciting illumination, so as to enable guidewire 21 to be used for a photoluminescent investigation. In one embodiment the photo-exciting illumination has a wavelength in the near ultra-violet, of approximately 370 nm, and the excited wavelength is in the visible spectrum. Typically, the photo-exciting illumination is radiated from one of fiber optics 160, 162, and the other fiber optic is used to check for any returning photoluminescent illumination. The transmission of the exciting illumination, and receiving of the excited photoluminescent illumination, are typically separated because the intensity of the photoluminescent illumination may be very low, and the receiving fiber optic permits filtering out of the exciting wavelength.

Figure 3:
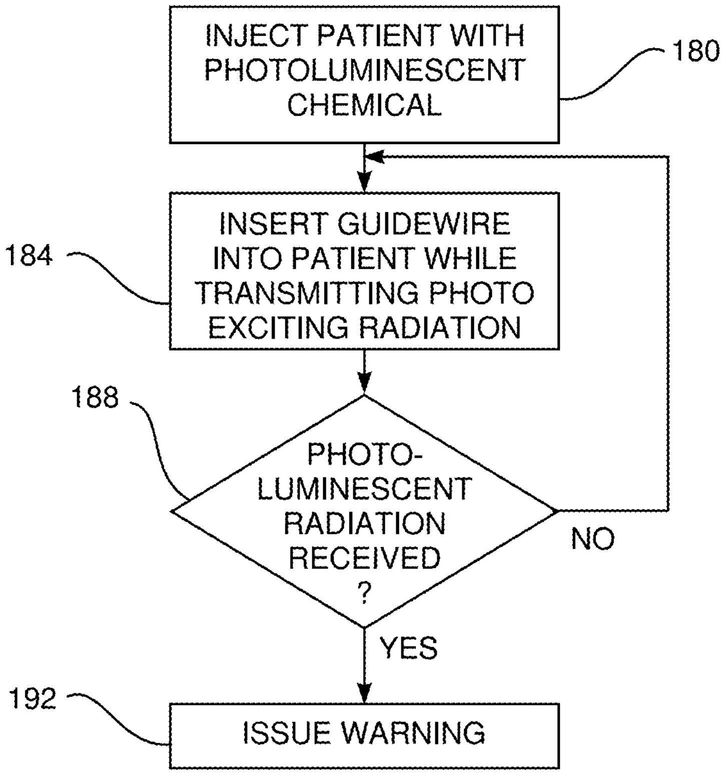
FIG. 3 is a flowchart describing steps for the guidewire to be used for a photoluminescent investigation, according to an embodiment of the present invention.

FIG. 3 is a flowchart describing steps for guidewire 21 to be used for a photoluminescent investigation, according to an embodiment of the present invention. By way of example, the investigation is assumed to provide physician 54 with a warning that the distal end of guidewire 21 is close to sensitive tissue, such as, as is assumed here, blood vessels close to the eye, so that the vessels are avoided.

In an initial step 180, patient 22 is injected with photoluminescent chemical that is known to be taken up by the blood vessels to be avoided.

In an insertion step 184, the physician inserts the distal end of guidewire into patient 22. On insertion, the physician activates optics module 46 to transmit photo-exciting illumination. Also on insertion, the physician activates tracking module 60 to track, using signals from sensor 28, the location and orientation of distal end of the guidewire. Typically, as is described below, CT image 64 of the patient is registered with the frame of reference of magnetic radiator assembly 24. In this case the location and orientation of the distal end of the guidewire may be combined with the registered CT image, and the combined image may be presented to the physician on screen 56.

In a condition 188, optics module 46 checks if photoluminescent radiation is received. If such radiation is received, indicating that the distal end of the guidewire is close to blood vessels that have taken up the injected photoluminescent chemical, then control transfers to a warning step 192. In step 192, a warning is presented to the physician, such as by processor 40 providing a notice on screen 56, and/or providing an audio signal.

If in condition 188 no photoluminescent radiation is received, control returns to step 184.

Impedance/Pacing Module 44

A pair of biocompatible electrodes 200, 204 are formed at the distal end of guidewire 21 on the outside of tube 70, typically as is illustrated in FIG. 2A, as annular rings. Electrodes 200, 204 are connected by conductive cabling (not shown in the figures) to impedance/pacing module 44, and the module is configured to operate in one of two modes, so as to investigate characteristics of tissue contacted by the electrodes. Both modes are described below.

Figure 4:
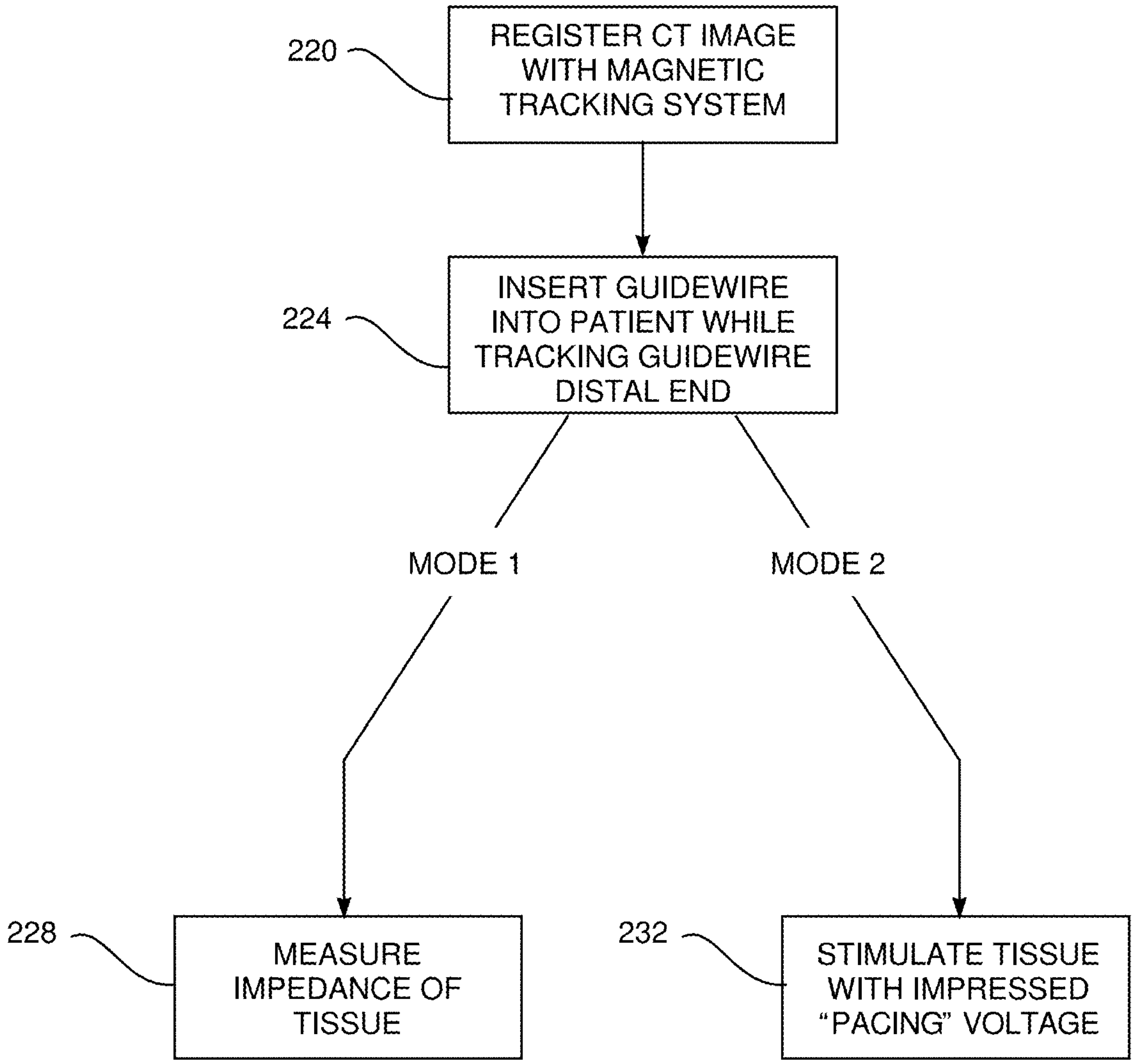
FIG. 4 is a flowchart describing steps for the guidewire to be used for a tissue characterization investigation using electrodes, according to an embodiment of the present invention.

FIG. 4 is a flowchart describing steps for guidewire 21 to be used for a tissue characterization investigation using electrodes 200, 204, according to an embodiment of the present invention.

In an initial registration step 220, CT image 64 of the patient is registered with the frame of reference of magnetic radiator assembly 24. The registration may be by any convenient method known in the art, such as by touching, with a wand having a magnetic sensor, external features of the patient that are identifiable in the CT image.

In an insertion step 224 physician 54 inserts guidewire 21 into patient 22, and tracks the position of the distal end. Because of the registration performed in the initial step, the tracking may be conveniently implemented by an icon of the distal end being overlaid on CT image 64, with the combined image (of the icon and initial CT image) being presented to the physician on screen 56. In addition, the physician is able to ascertain the position of the distal end using the image generated by camera 140, which is also typically presented on screen 56.

Once the distal end is at a location selected by the physician, the physician then activates the impedance/pacing module in one of two modes.

In an impedance measuring step 228, corresponding to a first mode of operation of module 44, the module measures the impedance of tissue contacted by both electrodes. Typically, in order to measure tissue impedance, module 44 applies a predetermined voltage at a predetermined frequency between electrodes 200, 204, and records the current transferred between the electrodes. As is known in the art, the impedance of tissue gives an indication as to whether the tissue is vital or fibrotic, and typical values of the impedance of different types of tissue may be found at www.ncbi.nlm-.nih.gov/pmc/articles/PMC5006502. In one embodiment, the frequency used is approximately 480 kHz, which is biocompatible and which does not stimulate the tissue, and the voltage is approximately 10 mV.

Alternatively, in a pacing step 232, corresponding to a second mode of operation of module 44, the module is used to electrically stimulate tissue contacted by electrodes 200 and 204. The stimulation is typically in the form of pulses, having a frequency somewhat higher than the heart rate of the patient, and an amplitude of approximately 14V.

If the stimulated tissue is vital, there is typically physical motion of the tissue, and/or a noticeable feeling by patient 22. Thus, if patient 22 has not been anesthetized, the patient may be able to tell the physician that he/she can feel the stimulation. Alternatively, for example if the patient is anesthetized, visible motion of vital tissue on stimulation may be apparent in an image generated by camera 140.

Image Combining Module 62

Image combining module 62 is configured to combine the image produced by camera 140 with the stored CT image 64 of the patient in one of two modes, as is explained below. The combination in each mode is typically performed automatically by processor 40, and both modes may be implemented substantially simultaneously. Typically during an investigation the physician chooses one, both, or neither mode.

A first mode enhances the "raw" image corresponding to stored CT image 64, and a second mode enhances the "raw" image generated by camera 140. Either or both of the enhanced images may typically be presented to the physician on screen 56, and the production of both types of enhanced image is described below.

Figure 5:
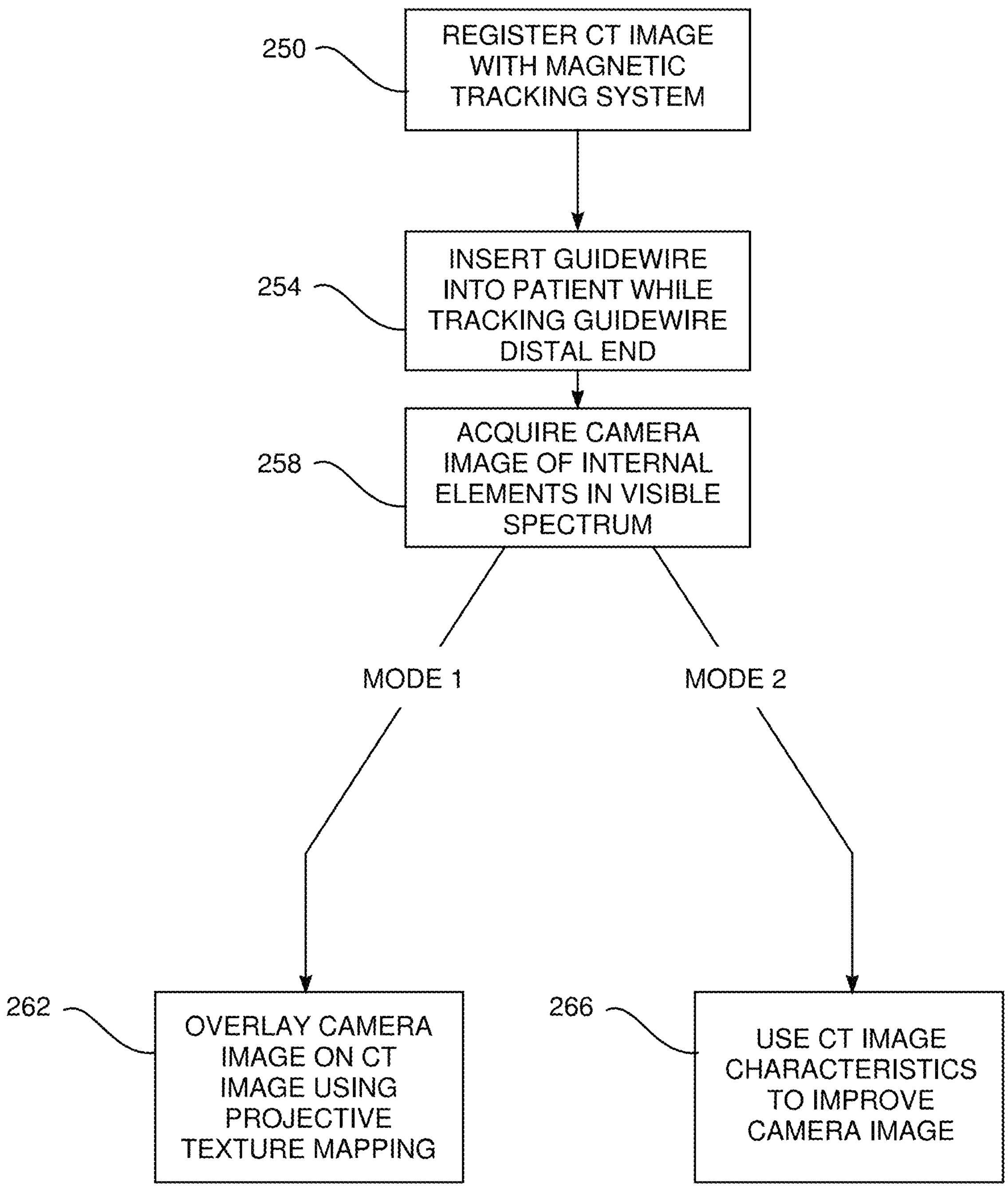
FIG. 5 is a flowchart describing steps for the guidewire to be used for enhancement of an image generated by a camera, according to an embodiment of the present invention.

FIG. 5 is a flowchart describing steps for guidewire 21 to be used for enhancement of the image generated by camera 140, according to an embodiment of the present invention.

An initial registration step 250, and an insertion step 254, are substantially as described above for steps 220 and 224 in the flowchart of FIG. 4.

In an camera image acquisition step 258, module 62 acquires and stores the image generated by camera 140.

In a CT image enhancement step 262, corresponding to the first mode, processor 40 and the image combining module overlay the two dimensional (2D) camera image onto the three dimensional (3D) voxels of CT image 64, using projective texture mapping. The overlay is possible because processor 40 is aware of the location and orientation of camera 140, and thus of its image, with respect to stored CT image 64, because of the registration performed in step 250, and from analysis of the signals of sensor 28.

The overlay transforms a 3D image corresponding to CT image 64 (which shows the correct 3D structure absent lighted surfaces, and typically uses artificial coloring set by the software) into a 3D image which combines the full 3D structure with coloring of an image acquired by the real-time camera. The image from the real-time camera not only replaces the artificial coloring, but also adds in detail from the 2D camera image, such as blood or other fluid, that is not in the CT image.

Figure 6:
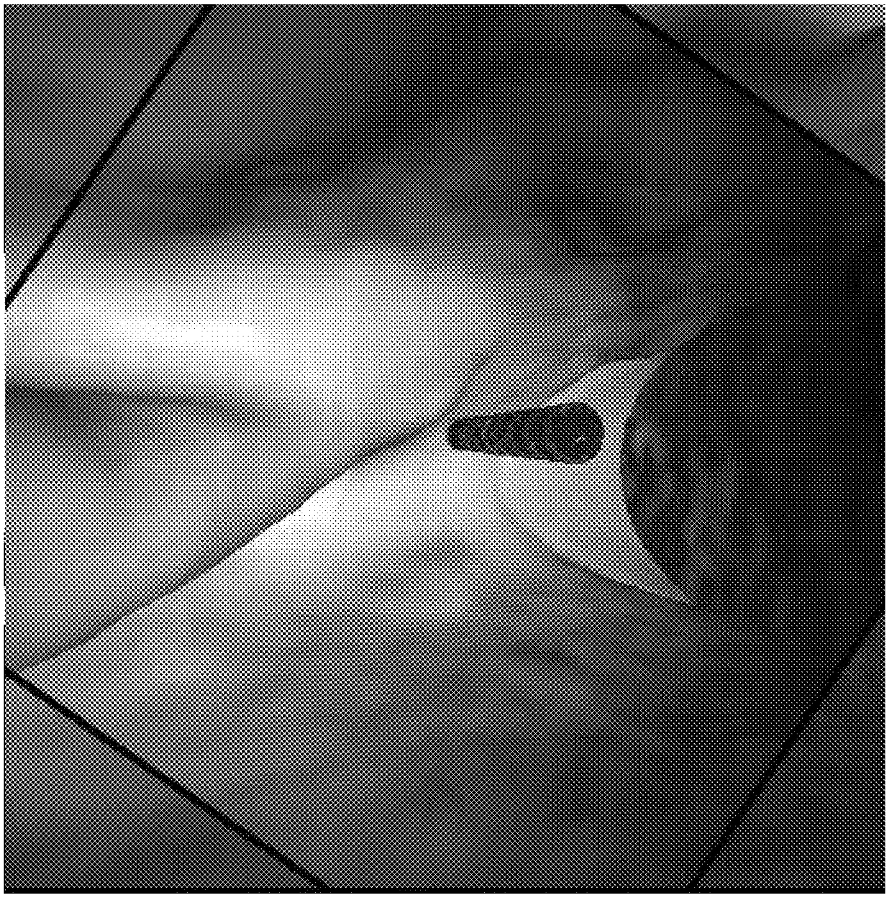
FIG. 6 is a schematic illustration of results of a first mode of enhancement of an image, according to an embodiment of the present invention.

FIG. 6 is a schematic illustration of the results of the first mode, according to an embodiment of the present invention.

In a camera image enhancement step 266, corresponding to the second mode, processor 40 and the image combining module analyze the two dimensional (2D) camera image acquired in step 258. Camera 140 has, by virtue of its size, relatively simple optics, so that the quality of the image formed is, inter alia, strongly dependent on the illumination of the object being imaged. Typically, objects that are distant from the camera are more poorly illuminated than those that are closer. In addition, since the pixels forming the camera image are of equal sizes, objects that are distant from the camera have a lower resolution than those that are closer to the camera.

In step 266 the processor is able to estimate the distance of elements of a scene imaged by the camera from the camera, since from registration step 250 and from analysis of the signals of sensor 28 the processor knows the position and orientation of the camera and its image with respect to the CT image. In addition, the processor is able to analyze the pixels of the camera image to estimate a value of the illumination forming each pixel.

To enhance the camera image the processor incorporates elements of the stored CT image 64 into the camera image. The incorporation typically comprises using 3D information from each pixel of the CT image (i.e., so as to determine an orientation of the surfaces and the normals of sections of the relevant image). The pixel color may then be manipulated with virtual light calculations using the normal retrieved from the 3D image so as to get an enhanced illuminated 2D image.

The enhanced illuminated 2D image enables better understanding of the 3D object observed with the camera, by compensating for the lack of enough illumination with true 3D geometry-lighting calculations.

The incorporation referred to above is typically on a weighted basis. Thus, for pixels having a low illumination more detail of the CT image is incorporated into the camera image compared to those having a high illumination. Similarly, for portions of the image that have a low resolution, typically those that are distant from the camera, more detail of the CT image is incorporated into the camera image compared to those having a high resolution.

Figure 7B:
FIGS. 7A and 7B are schematic illustrations of results of a second mode of the enhancement, according to an embodiment of the present invention.
Figure 7A:
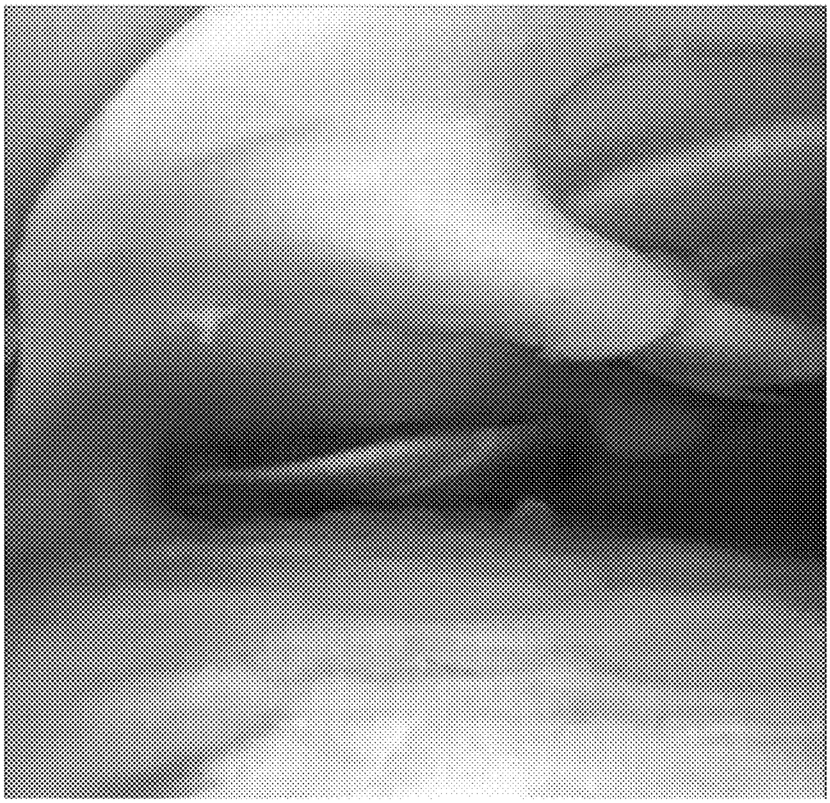

FIGS. 7A and 7B are schematic illustrations of the results of the second mode, according to an embodiment of the present invention. FIG. 7A illustrates the "raw" camera image; FIG. 7B illustrates the enhanced image.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method, comprising:

inserting a guidewire, comprising a flexible biocompatible tube having a tube distal end and a pair of biocompatible electrodes formed on an outer surface of the flexible biocompatible tube at the tube distal end, into an orifice of a body of a living subject so that the electrodes contact tissue therein;

applying pulses via the electrodes at a frequency greater than a heart rate of the living subject, so as to electrically stimulate the contacted tissue; and in response to the stimulation, providing an indication if the tissue is vital, wherein the indication comprises observing visible motion of the contacted tissue.

2. The method according to claim 1, further comprising:

tracking a position of the camera within the body with a camera fixed in proximity to the distal end;

acquiring an image of internal elements of the body with the tracked camera;

in response to the tracked position of the camera, combining the image of the internal elements with a computerized tomographic (CT) image of the internal elements so as to form a combined image; and presenting a combined image on a screen.

3. The method according to claim 2, wherein combining the image comprises overlaying the camera image onto the CT image using projective texture mapping.

4. The method according to claim 2, wherein combining the image comprises incorporating three-dimensional information derived from pixels of the CT image into the camera image.

5. The method of claim 1, wherein the guidewire further comprises a first and a second fiber optic having distal ends located in proximity to the tube distal end and wherein the method further comprises:

radiating photo-exciting illumination via the first fiber optic into the body;

receiving, via the second fiber optic, returning excited photoluminescent illumination after filtration of the photo-exciting illumination; and providing an indication of reception of the returning excited photoluminescent illumination.

6. The method according to claim 5, wherein the indication is indicative of the tube distal end being in proximity to tissue of the body that has taken up an injected photoluminescent chemical.

7. The method according to claim 1, wherein the method further comprises:

applying a predetermined voltage via the electrodes to the contacted tissue;

measuring a current generated in response to the predetermined voltage so as to measure an impedance of the contacted tissue; and providing an indication if the tissue is vital or fibrotic in response to the impedance.

8. The method according to claim 7, wherein the predetermined voltage is applied at a frequency which does not stimulate the tissue.

* * * * *